United States Patent
Margolis et al.

(10) Patent No.: US 8,415,289 B2
(45) Date of Patent: Apr. 9, 2013

(54) BACTERIAL-DERIVED BLIS FOR TREATMENT OF ACNE

(75) Inventors: David Margolis, Bala Cynwyd, PA (US); Whitney Bowe, Brooklyn, NY (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 12/086,335

(22) PCT Filed: Dec. 13, 2006

(86) PCT No.: PCT/US2006/047394
§ 371 (c)(1),
(2), (4) Date: Nov. 2, 2009

(87) PCT Pub. No.: WO2007/070518
PCT Pub. Date: Jun. 21, 2007

(65) Prior Publication Data
US 2010/0056423 A1    Mar. 4, 2010

Related U.S. Application Data

(60) Provisional application No. 60/749,633, filed on Dec. 13, 2005.

(51) Int. Cl.
*A61K 38/00* (2006.01)
*A01N 37/18* (2006.01)
*A61P 31/04* (2006.01)
*A61P 17/00* (2006.01)

(52) U.S. Cl.
USPC .............................. 514/1.1; 514/2.4; 514/18.6

(58) Field of Classification Search .................. None
See application file for complete search history.

(56) References Cited

U.S. PATENT DOCUMENTS

| 4,011,313 | A | * | 3/1977 | Thompson | 514/153 |
|---|---|---|---|---|---|
| 4,668,506 | A | | 5/1987 | Bawa | |
| 4,713,224 | A | | 12/1987 | Tamhankar | |
| 4,931,279 | A | | 6/1990 | Bawa | |
| 2002/0128186 | A1 | | 9/2002 | Hillman et al. | |
| 2003/0096365 | A1 | | 5/2003 | Faye et al. | |
| 2004/0038379 | A1 | | 2/2004 | Collins et al. | |
| 2004/0232205 | A1 | | 11/2004 | Tagg et al. | |
| 2005/0180963 | A1 | * | 8/2005 | Adams et al. | 424/93.45 |

FOREIGN PATENT DOCUMENTS

| EP | 1 060 745 | * | 12/2000 |
|---|---|---|---|
| WO | WO 98/35014 | * | 8/1998 |
| WO | WO 01/27143 | * | 4/2001 |

OTHER PUBLICATIONS

Burkhart et al. Acne: a review of immunologic and microbiologic factors. Postgrad Med J, 1999, vol. 75, pp. 328-331.*
Levy et al. Effect of Antibiotics on the Oropharyngeal Flora in Patients with Acne. Arch Dermatol. 2003, vol. 139, pp. 467-471.*
WEscombe et al. Purification and Characterization of Streptin, a Type A1 Lanbiotic Produced by Streptococcus pyogenes. Appl. Environ. Microbiol. 2003. vol. 69, No. 5, pp. 2737-2747.*
Pag et al., "Multiple activities in lantibiotics—models for the design of novel antibiotics?" Current Pharmaceutical Design, Apr. 2002, 8(9): 815-833.
Seppala H, Klaukka J, Vuopio-Varakila A et al and the Finnish Study Group for Antimicrobial Resistance. The effect of changes in the consumption of macrolide antibiotics on erythromycin resistance in group A streptococci in Finland. *N Engl J Med*. 1997;337:441-446.
York MK, Gibbs L, Perdreau-Remington F, Brooks GF. Characterization of antimicrobial resistance in *Streptococcus pyogenes* isolates from the San Francisco Bay area of Northern California. *J Clin Micro*. 1999;37:1727-1731.
Espersen F. Resistance to antibiotics used in dermatological practice. *Br J Dermatol*. 1998;139:4-8.
Leyden JJ, McGinley KJ, Cavalieri S, Webster GF, Mills PH, Kligman AM. *Propioibacterium acnes* resistance to antibiotics in acne patients. *J Am Acad Derm*. 1983;8:41-45.
Marples RR, Kligman AM. Ecological effect of oral antibiotics on the microflora of human skin. *Arch Derm*. 1971;103:148-153.
Miller YW, Eady EA, Lacey RW, Cove JH, Joanes DN, Cunliffe WJ. Sequential antibiotic therapy for acne promotes the carriage of resistant staphylococci on the skin of contacts. *J Antimicrobiol Chemother*. 1996;38:829-837.
Adams SJ, Cunliffe WJ, Cooke EM. Long-term antibiotic therapy for acne vulgaris: effects on the bowel flora of patients and their relatives. *J Invest Derm*. 1985;85:35-37.
Klaenhammer, "Genetics of bacteriocins produced by lactic acid bacteria", FEMS Microbiology Reviews 12, 1993, pp. 39-86.
Nes et al., "Biosynthesis of bacteriocins in lactic acid bacteria" Antonia Van Leeuwenhoek, Oct. 1996;70(2-4):113-28.
Nes et al., "Novel lantibiotics and their pre-peptides", Antonie Van Leeuwenhoek. Feb. 1996;69(2):89-97.
Langer, "New methods of drug delivery", Science 249:1527-1533 (1990).
Treat et al., in *Liposomes in the Therapy of Infectious Disease and Cancer*, Lopez-Berestein and Fidler (eds.), Liss, New York, pp. 353-365 (1989).
Lopez-Berestein, "Treatment of systematic fungal infections with liposomal-amphotericin B", pp. 317-327, 1989.
Abuchowski et al. "Immunosuppressive properties and circulating life of Achromobacter glutaminase-asparaginase covalently attached to polyethylene glycol in man" Cancer Treat Rep. 65(11-12): 1077-81 1981.
Katre et al. "Chemical modification of recombinant interleukin 2 by polyethylene glycol increases its potency in the murine Meth A sarcoma model" Proc Natl Acad Sci U S A. 84(6):1487-91. Mar. 1987.

(Continued)

*Primary Examiner* — Marcela M Cordero Garcia
(74) *Attorney, Agent, or Firm* — Mark S. Cohen; Pearl Cohen Zedek Latzer, LLP

(57) ABSTRACT

This invention relates to a treatment of acne. Specifically, the invention is directed to the use of bacteriocin-like inhibitory substances (BLIS), isolated from *S. salivarius* as bactericide or bacteriostat for acne-causing bacteria, namely *P. acnes*.

18 Claims, No Drawings

OTHER PUBLICATIONS

Buchwald et al. "Long-term, continuous intravenous heparin administration by an implantable infusion pump in ambulatory patients with recurrent venous thrombosis."Surgery 88:507 (1980).

Saudek et al."A preliminary trial of the programmable implantable medication system for insulin delivery." N. Engl. J. Med. 321:574 (1989).

Goodson, in Medical Applications of Controlled Release, supra, vol. 2, pp. 115-138 (1984).

Sefton, "Implantable pumps", CRC Crit. Ref. Biomed. Eng. 14:201 (1987).

* cited by examiner

BACTERIAL-DERIVED BLIS FOR TREATMENT OF ACNE

CROSS-REFERENCE TO RELATED APPLICATIONS

This application is a National Phase Application of PCT International Application No. PCT/US06/47394, International Filing Date Dec. 13, 2006, claiming priority of U.S. Provisional Patent Application 60/749,633, filed Dec. 13, 2005, now expired, both of which are incorporated herein by reference in their entirety.

GOVERNMENT INTEREST STATEMENT

This invention was made with government support under Grant Numbers HS10399 and AR02212, awarded by the National Institutes of Health. The government has certain rights in the invention.

FIELD OF INVENTION

This invention is directed to a treatment of acne. Specifically, the invention is directed to the use of bacteriocin-like inhibitory substances (BLIS), isolated from S. salivarius as bacteriocide or bacteriostat for acne-causing bacteria, namely P. acnes.

BACKGROUND OF THE INVENTION

Acne is an illness that afflicts adolescents and young adults. It has severe psychosocial consequences. About 20% of those with acne who seek medical care are severe enough to require systemic therapy. Based on NHANES, data about 2 million people per year are in this category, and they account for 5 to 6 million physician office visits per year. According to IMS, about 9.7 million prescriptions are written for oral and about 8.2 million prescriptions are for topical antibiotic therapy for acne yearly. Furthermore, the topicals are used as first line therapy 58% of the time and the orals 40% of the time. Therapy frequently continues for more than 6 months. Simply stated, very large quantities of antibiotics are used for an extended period of time by this sector of the population. GAS is an important public health issue in that it is the main bacterial cause for the more than 200 million cases of upper respiratory tract infections in the USA per year and the main reason to treat these cases with an antibiotic. The economic cost to the US alone is more than 25 billion dollars per year.

Individuals with acne are generally healthy patients often exposed to antibiotics for prolonged periods of time. It is believed that appropriate but long-term use of antibiotics by patients and physicians has played a role in the development of organisms that are now resistant to multiple antibiotics. Importantly, these changes are not always permanent. For example, reductions in the use of antibiotics have been shown to result in subsequent decreases in bacterial resistance of such organisms as *Streptococcus pyogenes* (Seppala H, Klaukka J, Vuopio-Varakila A et al and the Finnish Study Group for Antimicrobial Resistance. The effect of changes in the consumption of macrolide antibiotics on erythromycin resistance in group A streptococci in Finland. *N Engl J Med* 1997; 337:441-446; York M K, Gibbs L, Perdreau-Remington F, Brooks G F. Characterization of antimicrobial resistance in *Streptococcus pyogenes* isolates from the San Francisco Bay area of Northern California. *J Clin Micro.* 1999; 37:1727-1731). Tetracyclines and erythromycin are two antibiotics commonly used in dermatological practice for the long-term treatment of acne vulgaris (Espersen F. Resistance to antibiotics used in dermatological practice. *Br J Dermatol.* 1998; 139:4-8). Studies have shown that *Propionibacterium acnes* and coagulase-negative staphylococci quickly develop resistance to these antibiotics (Leyden J J, McGinley K J, Cavalieri S, Webster G F, Mills P H, Kligman A M. *Propionibacterium acnes* resistance to antibiotics in acne patients. *J Am Acad Derm.* 1983; 8:41-45; Marples R R, Kligman A M. Ecological effect of oral antibiotics on the microflora of human skin. *Arch Derm.* 1971; 103:148-153), which may result in therapeutic failure and the propagation of resistance to bacteria in the skin (Miller Y W, Eady E A, Lacey R W, Cove J H, Joanes D N, Cunliffe W J. Sequential antibiotic therapy for acne promotes the carriage of resistant staphylococci on the skin of contacts. *J Antimicrobiol Chemother.* 1996; 38:829-837) and gastrointestinal flora of close contacts (Adams S J, Cunliffe W J, Cooke E M. Long-term antibiotic therapy for acne vulgaris: effects on the bowel flora of patients and their relatives. *J Invest Derm.* 1985; 85:35-37). While the effects of long-term antibiotic use on cutaneous microbial environments in this patient population have been well studied, the effects of antibiotic use on non-cutaneous surfaces, such as the oro-pharynx, which could be a source of systemic illness, have not.

The injudicious use of antibiotics has been a public health concern for many years; as recently reinforced by a study on the potential association between antibiotics (including those used to treat acne) and breast cancers. Antibiotic drugs select for resistant bacterial pathogens and eliminate normal host flora, resulting in colonization and infection with drug-resistant pathogenic organisms. Fortunately, these changes are not always permanent. For example, stopping antibiotic use has been shown to result in both the subsequent resurgence of the sensitive organisms and the return of normal flora. While public health experts have frequently blamed this disturbing trend on injudicious antibiotic use, it should be noted that this phenomena can happen with appropriate antibiotic prescribing by physicians and, by patients, using antibiotics as recommended.

Acne vulgaris is a disease for which long-term antibiotic use is standard and appropriate therapy. However, the burden of both acne and acne therapies, as with all skin diseases, on society and the patient has not been well described (http://www.niams.nih.gov/ne/reports/sci_wrk/2002/Burden_skin_disease_MAIN.htm). Therefore, there is a need for effective treatment for Acne that will not be burdensome on society and the patient.

SUMMARY OF THE INVENTION

In one embodiment, the invention provides a method of treating acne of a subject, comprising administering to said subject, an effective amount of a bacteriocin-like inhibitory substance (BLIS), thereby treating said acne.

In another embodiment, the invention provides a method of treating acne of a subject, comprising administering to said subject an effective amount of a pharmaceutical preparation comprising a bacteriocin-like inhibitory substance (BLIS), whereby said BLIS is bacteriocidal or bacteriostatic for an acne-causing bacteria thereby treating said acne.

In one embodiment, the invention provides a method of suppressing, inhibiting the growth of, or killing a P. acnes bacteria comprising the step of contacting said bacteria with a bacteriocin-like inhibiting substance (BLIS), wherein said BLIS is a bacteriocide or a bacteriostat of P. acnes.

DETAILED DESCRIPTION OF THE INVENTION

This invention relates in one embodiment to the treatment of Acne with Bacteriocin-like inhibitory substances (BLIS).

The rapid rise of resistant bacterial pathogens has launched the search for alternative methods for combating infection. One of the biggest problems associated with antibiotics is their broad spectrum of activity. Many of these drugs exert an intensive selection pressure on both pathogenic and commensal bacteria, leading to antibiotic resistance. Concern regarding the overuse of antibiotics has been ubiquitous among both the scientific and lay community.

In one embodiment, the term "BLIS" refers to bacteriocin-like inhibitory substances, could serve as a natural alternative to antibiotics. In an attempt to prevent the overuse of antibiotics, physicians are being encouraged to only prescribe antibiotics when they are clearly indicated. Simultaneously, the pharmaceutical industry continues to allocate significant research and developmental funding to discover and potentially market new, sophisticated antibiotics that prove effective in treating multi-resistant organisms. The inventors have developed and are describing herein a technique to reliably isolate and culture a naturally-occurring alternative to antibiotics that show in one embodiment a treatment for acne, have a narrow spectrum of killing activity, and are a "natural" product of the normal human oral microbiota.

According to this aspect of the invention and in one embodiment, the invention provides a method of treating acne of a subject, comprising administering to said subject, an effective amount of a bacteriocin-like inhibitory substance (BLIS), thereby treating said acne In one embodiment, the invention provides a method of treating acne in a subject, comprising administering to said subject, an effective amount of a bacteriocin-like inhibitory substance (BLIS), whereby said BLIS is bacteriocidal or bacteriostatic for an acne-causing bacteria thereby treating said acne.

In one embodiment, $S.$ $salivarius$ strains ribosomally produce from gene-encoded precursor peptides, a form of BLIS that is able to inhibit both group-A streptococci (GAS) and $P.$ $acnes$ and towards which $S.$ $salivarius$ possesses a specific self-protection mechanism. In another embodiment, certain $S.$ $salivarius$ strains produce a form of BLIS that successfully inhibits GAS, but is unable to inhibit $P.$ $acnes$. In another embodiment, certain $S.$ $salivarius$ strains produce a form of BLIS capable of inhibiting $P.$ $acnes$, but are incapable of inhibiting GAS. In another embodiment, subsets of the $S.$ $salivarius$ strains are resistant to antibiotics described herein and are still capable of producing BLIS.

In one embodiment, the bacteria subset acquire the resistance to clindamycin, erythromycin and tetracycline by spontaneous mutation, or by transformation, plasmid flit between bacteria of various types, or a combination thereof in other embodiment In one embodiment, resistance to all antibiotics is obtained through transfer of gene cassettes, referring in one embodiment to genes that can be spliced in the chromosomes. In one embodiment, integrons code for integrases that can splice gene cassettes into chromosomes or other genetic material in the guest bacteria, where they become functional. In one embodiment, $S.$ $salivarius$ obtain resistance by accepting gene cassettes containing resistance to clindamycin, erythromycin and tetracycline, thereby acquiring resistance to these antibiotics.

In one embodiment, BLIS used in the methods and pharmaceutical preparations according to the invention are isolated from $S.$ $salivarius$ strains obtained from a subject or pool of subjects exhibiting acne, such as in one embodiment, adult onset acne, or in another embodiment pregnancy-related acne, or in another embodiment, juvenile acne. In one embodiment, BLIS used in the methods and pharmaceutical preparations according to the invention are isolated from $S.$ $salivarius$ strains obtained from a subject or pool of subjects, wherein the subject or pool of subjects has an antibiotic resistant strain of $S.$ $salivarius$.

$P.$ $acne$ is a gram-positive, non-spore forming, anaerobic rod bacteria. It is a common resident of the skin's pores and can also live in the oil glands of the human skin. In the pore, it resides at the bottom of the pore where the oil duct comes in, since that is its food source namely the sebum or skin oil produced by the oil gland. $P.$ $acne$ bacteria release in one embodiment, lipases to digest the sebum produced by the oil gland and "delivered" to the pore. In another embodiment, the combination of enzymes and digestive products stimulates an intense local inflammation of the cells lining the pore. This inflammation then bursts the hair follicle or pore, especially when the pore opening has been clogged by a mixture of oil and dead skin cells, which has formed a hardened "blackhead." Once the pore bursts from the inflammation, a cyst may form under the skin, or a lesion may develop on the surface of the skin in the form of a pustule. In one embodiment, eliminating $P.$ $acnes$ presence using BLIS isolated from bacteria according to the methods of the invention, is effective in treating acne in a subject.

Microbes produce an array of microbial defense systems including classical antibiotics, lytic agents, exotoxins, lantibiotics and bacteriocins. One subtype antibiotic has been called BLIS. BLIS is produced by $Streptococcus$ $salivarius$, which is a facultative anaerobic ?-hemolytic $streptococcus$ from the viridans group. This organism commonly inhabits the throat and produces at least six different types of BLIS. $S.$ $salivarius$ is generally believed to be the main regulator of Group A. Streptococci (GAS).

In one embodiment, the BLIS produced by $S.$ $salivarius$ is a peptide represented by the amino acid sequence KRGSGWIATITDDCPNSVFVCC (SEQ ID NO. 1) or KKGSGWFATITDDCPNSVFVCC (SEQ ID NO. 2), KRGTGWFATITDDCPNSVFVCC (SEQ ID NO. 3), GGGVIQTISHECRMNSWQFLFTCCS (SEQ ID NO. 4), or their combination in other embodiments.

In one embodiment, bacteria included in group A Streptococci (GAS) are $S.$ $pyogenes.$ Bacteriocins refer in one embodiment to proteinaceous, bacteriocidal or bacteriostatic substances synthesized by bacteria with usually, a narrow spectrum of activity. They are secreted oligopeptides, proteins or protein complexes with antimicrobial activity against strains taxonomically related to the producer organism. The term bacteriocin-like inhibitory substance (BLIS) refers in another embodiment to antagonistic substances which are not completely defined or do not fit the typical criteria of bacteriocins. In one embodiment BLIS used in the methods and compositions of the invention, inhibit a wide range of both gram-positive and gram-negative bacteria as well as fungi.

In one embodiment, the BLIS used in the methods and compositions of the invention, is isolated from $S.$ $salivarius,$ $S.$ $pyogenes,$ $L.$ $salivarius$ or a combination thereof. In one embodiment, the BLIS isolated from $S.$ $salivarius,$ used to treat acne according to the methods and compositions of the invention is Salivaricin A2 (SAL A2), or in another embodiment, Salivaricin B (SAL B).

In one embodiment, the BLIS is isolated from $S.$ $pyogenes$ and in another embodiment, the BLIS isolated from $S.$ $pyogenes$ is streptin A1. In one embodiment, Streptococcin A-FF22 (SA-FF22), the inhibitory product of $S.$ $pyogenes$ strain FF22, has characteristics that are similar to those of nisin, the "prototype" of the lantibiotic class of bacteriocins produced by certain strains of $Lactococcus$ $lactis.$ In one embodiment, the BLIS is isolated from *L. salivarius* and the BLIS is Salivacin 140, ABP-118, or a combination thereof. In one embodiment, bacteriocins produced by lactic acid bacteria (LAB) are categorized into three or four classes (Klaenhammer, 1993; Nes et al., 1996), of which Class I and Class II are the most prevalent. Class I bacteriocins the so-called lantibiotics which are small heat-stable peptides that owe their name to the modified amino acids with intramolecular thioether rings, such as lanthionine and b-methyl-lanthionine, present in their structures. Class II bacteriocins refer in another embodiment to the small heat-stable non-lantibiotics and these are subdivided into three subcategories: IIa, pediocin-like bacteriocins with strong antilisterial effects and a conserved N-terminal consensus motif within the mature peptide; IIb, bacteriocins whose activity depends on the complementary activity of two peptides; and IIc, bacteriocins whose secretion is sec dependent (Klaenhammer, 1993; Nes et al., 1996).

In one embodiment, the methods of the invention used to treat acne in a subject further comprises the step of contacting said acne-causing bacteria with BLIS isolated from *S. aureus, P. acnes, B. melaninogenicus*, or a combination thereof. In one embodiment, the methods of the invention for treating acne in a subject, comprise the step of contacting acne-causing bacteria in the subject with BLIS isolated from *S salivarius* and *P. acnes*. In one embodiment the BLIS is salivaricin and acnecin, and their effect is both bacteriocidal and bacteriostatic for *P. acnes* strains, thereby treating acne in the subject.

In one embodiment, the methods of the invention for treating acne in a subject, further comprise the step of administering to said subject an effective amount of an additional agent, such as isotrenitoin, salicylic acid, witchazel or Benzoyl peroxide, topical retinoid, spironolactone, an oral contraceptive, azeleic acid, glycolic acid, topical antibiotics, sulfa-based antibiotics, spf/sunblock, moisturizers or a combination thereof in other embodiments. In one embodiment, the invention provides a method for treating acne in a subject, comprising contacting an acne—causing bacteria in said subject with BLIS isolated from *S. salivarius* and BLIS isolated from *S. aureus, P. acnes, B. melaninogenicus*, and topical retinoid or a combination thereof in the form of an ointment, or a cream or a gel, or a foam and additionally in an oral form, antibiotic such as erythromycin, tetracycline, doxycycline, minocycline, oxytetracycline clindamycin, or a combination thereof. A person skilled in the art will readily recognize that the components of any treatment composition may be adjusted and optimized based on the symptoms exhibited by the subject, their severity and potential synergistic or antagonistic interactions among the components of such treatment, without exceeding the scope of the invention.

In one embodiment, the methods and compositions of the invention are used as a supplementary treatment for acne. In one embodiment, the method of treating acne in a subject likely to become pregnant comprises the step of administering to said subject spironolactone, oral contraseptives and BLIS isolated from *S. salivarius*. In another embodiment, treatment with BLIS for other purposes, such as in a composition to treat the results of aging as in aging creams in another embodiment, while not the primary purpose of the use of BLIS is still encompassed by the methods and compositions described herein.

In another embodiment, the methods of the invention are used to treat a subject wherein the subject has been diagnosed with acne caused by acne-causing bacteria, which due in one embodiment to long exposure to antibiotics, has become resistant to that antibiotic. In another embodiment, the acne-causing bacteria sought to be terminated or inhibited is resistant to erythromycin, or tetracycline, doxycycline, minocycline, oxytetracycline clindamycin, or a combination thereof in other embodiments.

In one embodiment, prolonged exposure to topical antibiotics is associated with the least resistance of the BLIS forming *S. salivarius*, while oral antibiotics is associated with an intermediate level of resistance, and oral plus topical antibiotic therapy is associated with the most resistance.

In one embodiment, the methods of the invention described herein, are carried out by administering to the subject a pharmaceutical preparation comprising any of the embodiment described herein.

According to this aspect of the invention and in one embodiment, the invention provides a method of treating acne of a subject, comprising administering to said subject an effective amount of a pharmaceutical preparation comprising a bacteriocin-like inhibitory substance (BLIS), whereby said BLIS is bacteriocidal or bacteriostatic for an acne-causing bacteria thereby treating said acne.

In one embodiment, administering a pharmaceutical preparation according to the methods of the invention, comprises orally administering to said subject a liquid or solid formulation containing the pharmaceutical preparation, which in another embodiment, comprises BLIS or a cocktail of BLIS and other agents in other embodiments. In one embodiment, the pharmaceutical preparations of the invention are administered in a topical form, directly to acne lesions or pimples on the skin of the subject. In one embodiment, the pharmaceutical preparations of the invention are administered in a food product such as yoghurt in one embodiment, or other similarly suitable food product.

Topical administration of the compositions described herein, is done in one embodiment with foams, or glass microbeads in another embodiment.

Pharmaceutical preparations include those suitable for oral or parenteral (including in other embodiments intravenously, intraarterially, intratumorically or intramuscularly) administration. Forms suitable for parenteral administration also include forms suitable for administration by inhalation or insufflation or for nasal, or topical (including buccal, rectal, vaginal and sublingual) administration. The preparations may, where appropriate, be conveniently presented in discrete unit dosage forms and may be prepared by any of the methods well known in the art of pharmacy. Such methods include the step of bringing into association the active compound with liquid carriers, solid matrices, semi-solid carriers, finely divided solid carriers or combinations thereof, and then, if necessary, shaping the product into the desired delivery system.

Pharmaceutical preparations suitable for oral administration may be presented as discrete unit dosage forms such as hard or soft gelatin capsules, cachets or tablets each containing a predetermined amount of the active ingredient; as a powder or as granules; as a solution, a suspension or as an emulsion; or in a chewable base such as a synthetic resin or chicle for ingestion of the agent from a chewing gum. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art, i.e., with enteric coatings.

The methods of the present invention involves in one embodiment, administering to a subject a pharmaceutical preparation comprising BLIS isolated from *S. salivarius*. The pharmaceutical preparation can comprise BLIS isolated from

*S. salivarius* alone or can further include a pharmaceutically acceptable carrier and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing BLIS isolated from *S. salivarius* can be administered to a subject by, for example, subcutaneous implantation of a pellet in an area of the body closest to acne infection, such as shoulder in one embodiment. In another embodiment, the pellet provides for controlled release of BLIS isolated from *S. salivarius* over a period of time. The preparation can also be administered by intravenous, intra-arterial, or intramuscular injection of a liquid preparation, oral administration of a liquid or solid preparation, or by topical application. Administration can also be accomplished by use of a rectal suppository or a urethral suppository. The pharmaceutical preparation can also be a parenteral formulation; in one embodiment, the formulation comprises a liposome that includes a complex of BLIS isolated from *S. salivarius* such as, for example, salivaricin, salivaricin A2, salivaricin B or a combination thereof.

Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The preparations according to the invention may also be formulated for parenteral administration (e.g., by injection, for example, bolus injection or continuous infusion) and may be presented in unit dose form in ampules, pre-filled syringes, small volume infusion containers or in multi-dose containers with an added preservative. The preparations may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds may be formulated as ointments, gels, creams or lotions, or as the active ingredient of a transdermal patch. Suitable transdermal delivery systems are disclosed, for example, in A. Fisher et al., U.S. Pat. No. 4,788,603, or R. Bawa et al. U.S. Pat. Nos. 4,931,279; 4,668,506 and 4,713,224 all which are hereby incorporated by reference in their entirety. Ointments and creams are formulated in one embodiment with an aqueous or oily base with the addition of suitable thickening and/or gelling agents. Lotions are formulated in another embodiment with an aqueous or oily base and will contain in one embodiment, one or more emulsifying agents, stabilizing agents, dispersing agents, suspending agents, thickening agents, or coloring agents.

For topical administration to body surfaces using, for example, creams, gels, drops, and the like, BLIS isolated from *S. salivarius* or their physiologically tolerated functional derivatives such as salts, esters, N-oxides, and the like are prepared and applied as solutions, suspensions, or emulsions in a physiologically acceptable diluent with or without a pharmaceutical carrier. In another embodiment, the active compound can be delivered in a vesicle, in particular a liposome (see Langer, Science 249:1527-1533 (1990); Treat et al., in *Liposomes in the Therapy of Infections Disease and Cancer*, Lopez-Beresstein and Fidler (eds.), Liss, New York, pp. 353-365 (1989); Lopez-Beresstein, ibid., pp. 317-327; see generally ibid).

Preparations suitable for topical administration in the mouth include unit dosage forms such as lozenges comprising active ingredient in a flavored base, usually sucrose and acacia or tragacanth gums; pastilles comprising the active ingredient in an inert base such as gelatin and glycerin or sucrose and acacia gum; mucoadherent gels, and mouthwashes comprising the active ingredient in a suitable liquid carrier.

In one embodiment, the BLIS used in the methods of the invention is combined with other probiotic agents and delivered simultaneously. Probiotic supplements contain in one embodiment, bacteria that assist in balancing the levels of indigenous microorganisms in the subject's body. Probiotics are available in varied forms such as yogurt and other foods, capsules, tablets, beverages, and powders.

In one embodiment, the preparations described herein can be adapted to give sustained or controlled release of the active ingredient employed, e.g., by combination with certain hydrophilic polymer matrices, e.g., comprising natural gels, synthetic polymer gels or mixtures thereof. The polymer matrix can be coated onto, or used to form, a medical device, such as a patch, or the like.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms, protective coatings, protease inhibitors or permeation enhancers for various routes of administration, including parenteral, pulmonary, nasal and oral. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

In yet another embodiment, the pharmaceutical preparations can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity of the therapeutic target, i.e., the head, thus requiring only a fraction of the systemic dose (see, e.g., Goodson, in Medical Applications of Controlled Release, supra, vol. 2, pp. 115-138 (1984). Preferably, a controlled release device is introduced into a subject in proximity of the site of inappropriate immune activation or a tumor. Other controlled release systems are discussed in the review by Langer (Science 249:1527-1533 (1990).

Pharmaceutical preparations suitable for rectal administration wherein the carrier is a solid are in one embodiment, presented as unit dose suppositories. Suitable carriers include cocoa butter and other materials commonly used in the art, and the suppositories may be conveniently formed by admixture of the active compound with the softened or melted carrier(s) followed by chilling and shaping in molds.

Preparations suitable for vaginal administration may be presented as pessaries, tampons, creams, gels, pastes, foams or sprays containing, in addition to the active ingredient, such carriers as are known in the art to be appropriate.

Further, as used herein "pharmaceutically acceptable carriers" are well known to those skilled in the art and include, but are not limited to, 0.01-0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

In one embodiment, the pharmaceutical preparations used in the invention further comprise a carrier, or excipient, lubricant, flow aid, processing aid or diluent in other embodiments, wherein the carrier, excipient, lubricant, flow aid, processing aid or diluent is a gum, starch, a sugar, a cellulosic material, an acrylate, calcium carbonate, magnesium oxide, talc, lactose monohydrate, magnesium stearate, colloidal silicone dioxide or mixtures thereof.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetener, a film forming agent, or any combination thereof.

The pharmaceutical preparations of the invention can be prepared by known dissolving, mixing, granulating, or tablet-forming processes. For oral administration, the acridine, acridine derivative or their combinations or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin capsules aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant such as stearic acid or magnesium stearate. Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the acridine, acridine derivative or their combinations or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

An active component can be formulated into the composition as neutralized pharmaceutically acceptable salt forms. Pharmaceutically acceptable salts include the acid addition salts (formed with the free amino groups of the polypeptide or antibody molecule) and are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The active agent is administered in another embodiment, in a therapeutically effective amount. The actual amount administered, and the rate and time-course of administration, will depend in one embodiment, on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used in another embodiment, to deliver the active agent more specifically to certain types of cell, by the use of targeting systems such as antibodies or cell specific ligands. Targeting may be desirable in one embodiment, for a variety of reasons, e.g. if the agent is unacceptably toxic, or if it would otherwise require too high a dosage, or if it would not otherwise be able to enter the target cells.

The dosage regimen for treating acne with the cocktail therapy as described herein is selected in one embodiment, in accordance with a variety of factors, such as the type, age, weight, ethnicity, sex and medical condition of the subject, the severity of the acne condition, the route of administration, and the particular compound employed, and thus may vary widely without exceeding the scope of the invention.

In the practice of the embodiments of methods as described herein, an effective amount of compounds of the present invention or pharmaceutical preparations thereof, as defined herein, are administered via any of the usual and acceptable methods known in the art, either singly or in combination with another compound or compounds of the present invention or other pharmaceutical agents, such as salycilic acid, azeleic acid, glycolic acid, antibiotics such as, but not limited to topical antibiotics, sulfa-based anti-biotics; hormonal agents for the treatment of acne such as oral contraceptive or anti-androgen in certain embodiments, witchhazel spf/sunblock, moisturizers and so forth. The method of administering the active ingredients of the present invention is not considered limited to any particular mode of administration. The administration can be carried out in one embodiment, in single unit dosage form with continuous therapy or in another embodiment, in single dose therapy ad libitum. Other embodiments of administration are effective for treating the conditions acne. In other embodiments, the pharmaceutical preparation and method of the present invention are used when relief of symptoms is specifically required, or, in one embodiment, imminent. The compositions and method described herein are usefed in ones embodiment, as a continuous or prophylactic treatment.

In one embodiment, the term "treatment" refers to any process, action, application, therapy, or the like, wherein a subject, including a human being, is subjected to medical aid with the object of improving the subject's condition, directly or indirectly. In another embodiment, the term "treating" refers to reducing incidence, or alleviating symptoms, eliminating recurrence, preventing recurrence, preventing incidence, improving symptoms, improving prognosis or combination thereof in other embodiments.

"Treating" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. A method to treat adult-onset acne according to the invention, may comprise in one embodiment, a method to inhibit the growth of acne-causing bacteria such as $P.$ $acnes$, since the latter may lead to, or aggravate adult-onset acne.

The rapid rise of multi-resistant bacterial pathogens has made it necessary to identify alternative methods of combating infection as well as inflammatory conditions. In one embodiment, patients infected with resistant $P.$ $acnes$ strains have poorer clinical outcomes than patients infected with sensitive strains. BLIS serves in one embodiment as a natural alternative to antibiotics. Bacteriocins such as BLIS in one embodiment, have a relatively narrow spectrum of killing activity, resulting in a reduction in the intensity of selection for resistance. In one embodiment BLIS isolated from strains of $S.$ $salivarius$ capable of acting against both GAS and $P.$ $acnes$. Surprisingly this is the first time that the capability of $S.$ $salivarius$ to produce a substance inhibitory to $P.$ $acnes$ has been demonstrated. This substance is therefore a promising treatment for infections caused by GAS, such as pharyngitis and impetigo, as well as for acne.

According to this aspect of the invention and in one embodiment, the invention provides a method of suppressing, inhibiting the growth of, or killing a $P.$ $acnes$ bacteria comprising the step of contacting said bacteria with a bacteriocin-like inhibiting substance (BLIS), wherein said BLIS is a bacteriocide or a bacteriostat of $P.$ $acnes$ In one embodiment, the invention provides a method of inhibiting the growth of, or killing a $P.$ $acnes$ bacteria comprising the step of contacting said bacteria with a bacteriocin-like inhibiting substance (BLIS), wherein said BLIS is isolated from $S.$ $salivarius$, wherein said BLIS is a bacteriocide or a bacteriostat of $P.$ $acnes$.

In one embodiment, "contacting" a bacteria with a substance refers to (a) providing the substance to the environment of the bacteria (e.g., solution, in vitro culture medium, anatomic fluid or tissue) or (b) applying or providing the substance directly to the surface of the bacteria, in either to case, so that the substance comes in contact with the surface of the cell in a manner allowing for biological interactions between the bacteria and the substance.

In one embodiment, the term "subject" for purposes of treatment refers to a human subject who is susceptible to or suffering from acne. The subject, in one embodiment is at risk of or exhibiting symptoms associated with acne due to age, or exposure to bacterial infection, being pregnant being medicated (e.g. taking steroids) and the like.

The following examples are presented in order to more fully illustrate the preferred embodiments of the invention. They should in no way be construed, however, as limiting the broad scope of the invention.

EXAMPLES

Materials and Methods

Source Population and Study Design

A total of 106 male and female patients were recruited to participate in this cross-sectional study. This convenience sample of young, healthy individuals treated in the Department of Dermatology at the Hospital of the University of Pennsylvania was recruited without prior knowledge of their antibiotic use. The study was designed to determine the colonization and resistance pattern of $S.$ $salivarius$ in the oropharynx of two groups: Group I—subjects carrying the diagnosis of acne, whether or not they were using antibiotics (topical, oral or both); Group II—subjects not carrying the diagnosis of acne and thus not using antibiotics as part of their therapeutic regimen. Group I was further sub-divided into two groups: Group Ia: acne patients currently using antibiotics (topical and/or oral) as part of their acne therapy, and Group Ib: acne patients not currently (within the last 3 months) using antibiotics as part of their acne therapy. Our protocol was reviewed and given approval by the institutional review board of the Hospital of the University of Pennsylvania.

All subjects filled out a questionnaire, inquiring about the duration and type of any acne therapies used in the preceding three months. Individuals were excluded from the study if they had been seen by a physician and prescribed an antibiotic (oral or topical) for an upper respiratory tract infection (e.g. head cold, sore throat, bronchitis, flu, etc) or any other non-acne reason in the preceding three months. Individuals with previous upper respiratory tract infections not treated with antibiotics were included.

$Streptococcus$ $Salivarius$ Sampling, Growth and Identification

The dorsum of the tongue was swabbed and the specimen collected using a BBL CultureSwab Collection and Transport System (Difco, Detroit, Mich.). The sterile cotton stick was drawn across the dorsum of the tongue 10-12 times while maintaining pressure. Swabs were stored at 4° C. for no more than 24 h. Cultures were diluted 10 and 100-fold using Tryptic Soy Broth (Difco, Detroit, Mich.), and diluted cultures directly inoculated on mitis-salivarius agar (Difco, Detroit, Mich.) using sterile technique. Plates were incubated upside down at 37° C. in 5% carbon dioxide for 24 h. Colonies were screened by morphology consistent with $S.$ $salivarius$ (large, soft, fluffy colonies due to levan production from the sucrose in the agar). This is the standard method used to screen for $S.$ $salivarius$ (24;24). All samples identified based on visual morphology were frozen and stored for subsequent testing (BLIS assays and resistance testing).

PCR Analysis

A random sample (21/28) of these isolates was tested using PCR primers reported by Igarashi et al. (2001). These primers target the DNA sequence encoding the dextranase gene of $S.$ $salivarius$. Genomic DNA was obtained from the clinical isolates using QIAGEN Genomic-tip 20/G from QIAGEN Inc (Valencia, Calif.). Forward and reverse PCR primers, 5'-AACGTTGACCTTACGCTAGC-4' (SEQ ID NO. 1) and 5'-GATTCTOTCAAAGAA GCCAC-3' (SEQ ID NO. 2), respectively, were obtained from Integrated DNA Technologies (Coralville, Iowa). The Expand Long Template PCR System (Roche Diagnostic Corporation, Indianapolis, Ind.) was used. PCR reaction mixtures containing 50 ng of genomic DNA were denatured at 94° C. for 2 min followed by 10 cycles at 94° C. for 10 seconds, 53° C. for 30 seconds and 68° C. for 2 min and 20 cycles at 94° C. for 15 seconds, 53° C. for 30 seconds, 68° C. for 2 min (including a 20 second elongation step for each successive cycle). The last step was a 10 min incubation at 68° C. All PCR reactions were run in a Perkin Elmer thermal cycler. Amplified products were examined by electrophoresis on 1% agarose gels stained with ethidium bromide. Genomic DNA from *S. salivarius* ATCC 13419 and *S. pyogenes* ATCC 19615 were used as positive and negative controls. The positive control DNA yielded a PCR product of the expected size of 2271 kb.

Determination of Resistance

Colonies identified as *S. salivarius* by morphology were tested for susceptibility to clindamycin, erythromycin and tetracycline using the Etest MIC method. Etest strips were purchased from AB Biodisk (Piscataway, N.J., USA), and were used in accordance with the manufacturer's instructions. The concentration gradient of each antimicrobial agent on the Etest strips was 0.016-256 ug/ml. MICs were read directly from the test strip where the zone of inhibition intersected the MIC scale on the strip. Zones of inhibition were compared with standard values (NCCLS M100-S10) to assign a designation of "susceptible," "intermediate", or "resistant" to each antimicrobial agent.

Testing for BLIS Production; Testing for Inhibition of GAS by BLIS

Human clinical specimens of *S. salivarius* collected using the methods above and screened using morphology were subsequently evaluated for BLIS production using a modified deferred antagonism assay. Each *S. salivarius* isolate was considered a "producer strain." The isolates were grown aerobically in Bacto Tryptic Soy Broth, Soybean-Casein Digest Medium (BD Diagnostics, Sparks, Md.) and a cotton swab was charged with growth and used to inoculate a diametric streak across Columbia Blood Agar. Each plate was then incubated for 18 hours at 35° C. in 5% $CO_2$, and the resulting macroscopically visible growth removed with the edge of a glass slide. The plate was then inverted over chloroform vapors for 30 min, and subsequently exposed to air for 15 min. Three strains of group-A streptococci (ATCC 12344, 19615, and 12384) were used as indicator strains and streaked at right angles to the test streak. The plate was incubated anaerobically (BD BBL GasPak, Sparks, Md.) for 24 hours at 35° C. For the purposes of this study, bacterial inhibition was considered significant if the zone of inhibition of the indicator strain was as least twice the width of the original test streak. This clear zone of inhibition served as evidence that a clinical isolate of *S. salivarius* was able to produce BLIS, and that this BLIS was effective in inhibiting the growth of a strain of GAS. Isolates that inhibited any or all of the GAS strains were considered BLIS producers.

Testing for BLIS Production; Testing for Inhibition of *P. Acnes* by BLIS

The same deferred antagonism assay was repeated, substituting *P. acnes* for the GAS indicator strains. *S. salivarius* colonies were identified, grown, streaked and scraped according to the methods above. *Propionibacterium acnes* ATCC 6919 was streaked onto Columbia blood agar and incubated anaerobically for 72 h hours at 35° degrees C. Isolates were picked and grown anaerobically in soy broth, and streaked at right angles to the *S. salivarius* test streaks (see above). Plates were incubated anaerobically for 24 h at 35° C. Zones of inhibition at least twice the width of the original test streak served as evidence that a clinical isolate of *S. salivarius* was able to produce BLIS, and this particular BLIS was effective in inhibiting the growth of *P. acnes*.

Data Analysis

The primary objective was to estimate the prevalence of *S. salivarius* in the oral cavity of those with acne (Group I) and those without acne (Group II). Based on our hypothesis that *S. salivarius* would be affected by antibiotic exposure, we also then separately evaluated those with acne who were using antibiotic therapy (Group Ia) and those with acne, not using antibiotic therapy (Group Ib). Colonies of *S. salivarius* were identified visually by morphology and chi-squared analyses were performed to detect a difference among these groups. Pearson $chi^2$ P values were considered significant if they were less than 0.05.

Secondarily, determination was made as to whether the *S. salivarius* recovered was resistant to clindamycin, erythromycin, and tetracycline. Chi-squared analyses were performed to detect a difference among Groups Ia, Ib, and II. We further stratified the acne patients into those receiving oral and/or topical antibiotics, and no antibiotics. These findings were represented as simple percentages, allowing for qualitative comparisons among these groups. Five bacterial isolates, two from Group Ia, two from group Ib, and one from Group II, did not survive the freezing and thawing process and thus could not undergo susceptibility testing. This accounts for the discrepancy between the numerators in Table 2 and the denominators in Table 3.

Finally, those human clinical isolates of *S. salivarius* that produced BLIS were identified using both GAS standard reference strains (ATCC 19615, 12344, and 12384) and *P. acnes* standard reference strain ATCC 6919 as indicator strains. Of the 38 *S. salivarius* isolates identified via morphology, 33 survived to undergo testing for BLIS production. The percentage of BLIS-producing strains was determined according to the study group (Group Ia, Ib, or II) and according to the organism that was inhibited (GAS vs. *P. acnes*). Again, the same five bacterial isolates did not survive freezing and thawing to undergo BLIS testing.

All analyses were performed using STATA 8.2 (STATA Corporation, College Station, Tex.) or Statistical Package for the Social Sciences (SPSS) version 16 for Windows (SPSS, Inc., Chicago, Ill.).

Example 1

Exposure to Prolonged Antibiotics Treatment Selects for *S. ASalivarius* in the Ore-Pharynx of Patients without Acne The average (SD) age of 106 individuals was 27 (7.5) years, and 78% were female (Table 1). Overall, 77 subjects carried a diagnosis of acne (Group I), while 29 subjects did not (Group II). Of the 77 subjects carrying an acne diagnosis, 36 were currently using an oral and/or topical antibiotic (Group Ia), while the remaining 41 were not currently using any antibiotic therapy (Group Ib). Of those using antibiotics, 13 were using oral antibiotics only, 14 were using topical antibiotics only, and 9 were using both oral and topical antibiotics.

Based on visual morphology, of those without acne, 55% had *S. salivarius* cultured from their oro-pharynx. Of those with acne, 29% had *S. salivarius* cultured from their oro-pharynx (p=0.01 as compared to those without acne) (Table 2). Of the acne patients using antibiotic therapy, 42% had *S. salivarius* cultured from their oro-pharynx, while only 17% of the acne patients not exposed to antibiotic therapy had *S. salivarius* cultured from their oro-pharynx (p=0.06 comparing the two acne subgroups) (Table 2). The rate of recovery of *S. salivarius* between those without acne and those with acne on antibiotics was not statistically different (p=0.662). The prevalence of *S. salivarius* measured in acne patients using antibiotics was similar among those using oral antibiotics only, topicals only, and those using a combination of oral and topical antibiotic therapy.

TABLE 2

Prevalence of *Streptococcus salivarius* in the Oropharynx of Individuals Based on Acne diagnosis and Antibiotic Use

| Characteristic | Group Ia: Acne; Using Antibiotics | Group Ib: Acne; Not using Antibiotics | Group II: No Acne; No Antibiotics |
|---|---|---|---|
| Salivarius cultured (prevalence) | 15/36 (42%) α, β | 7/41 (17%) | 16/29 (55%) γ |

PCR, based on the detection of the dextranase gene sequence was conducted on a subgroup of specimens that had been visually confirmed to be *S. salivarius*. Of the morphologically-identified samples tested, 89% (23/26) were PCR positive. There was one instance when the PCR test was negative but the isolate produced BLIS.

Example 2

*S. Salivarius* in the Oro-Pharynx of Patients with Acne is Resistant to Antibiotics 69% of the *S. salivarius* cultures from acne patients using antibiotics were resistant to clindamycin and erythromycin, and 77% were resistant to tetracycline. 20%, 40% and 40% of acne patients not using antibiotics were resistant to clindamycin, erythromycin and tetracycline, respectively. Only 7%, 20% and 27% of *S. salivarius* cultures from patients without a diagnosis of acne were resistant to these same three antibiotics (Table 3). Interestingly, a trend in antibiotic resistance was detected when the mode of antibiotic administration was considered. Topical antibiotics appeared to be associated with the least resistance, oral antibiotics an intermediate level of resistance, and oral plus topical antibiotic therapy the most resistance.

TABLE 3

Proportion of Antibiotic-Resistant *Streptococcus salivarius* in the Oropharynx of Individuals Based on Acne diagnosis and Antibiotic Use*

| Resistance to: | Group Ia: Acne; Using Antibiotics | Group Ib: Acne; Not using Antibiotics | Group II: No Acne; No Antibiotics | P value |
|---|---|---|---|---|
| Clindamycin | 9/13 (69%) | 1/5 (20%) | 1/15 (7%) | 0.002 |
| Erythromycin | 9/13 (69%) | 2/5 (40%) | 3/15 (20%) | 0.031 |
| Tetracycline | 10/13 (77%) | 2/5 (40%) | 4/15 (27%) | 0.027 |

Example 3

*S. Salivarius* in the Oro-Pharynx of Patients with Acne Produce BLIS which Inhibits GAS and *P. Acnes*

13 of the 33 (39%) *S. salivarius* strains tested positive for BLIS production (using the traditional assay showing inhibition of GAS). 38% (5/13) of the *S. salivarius* isolates from acne patients on antibiotics were inhibitory to GAS, and thus considered BLIS-producing. A similar pattern of BLIS production and GAS inhibition was found for 20% (1/5) of *S. salivarius* isolates from acne patients not on antibiotics, and 47% (7/15) of subjects without acne. When tested for the production of a (BLIS-like) substance resulting in *P. acnes* inhibition, 54% (7/13) of acne patients using antibiotics, 20% (1/5) of acne patients not using antibiotics, and 20% (3/15) of subjects without acne tested positive. 52% (17 of the 33) *S. salivarius* isolates were capable of producing some form of inhibitory substance, thereby testing positive in at least one of the two deferred antagonism assays. Five of these 17 *S. salivarius* strains produced a form of BLIS that was able to inhibit both GAS and *P. acnes*. Seven of these strains produced a form of BLIS that successfully inhibited GAS, but was unable to inhibit *P. acnes*. Five of the 17 strains produced a form of BLIS capable of inhibiting *P. acnes*, but incapable of inhibiting GAS. A subset of the *S. salivarius* strains found to be resistant to each of the antibiotics tested were still capable of producing BLIS.

Example 4

Colonization of *Streptococcus Pyogenes* and *Staphylococcus Aureus* in the Oropharynx of a Young Adult Population is Higher than Previously Reported While much work has been done investigating the presence of pathogenic bacterial organisms in the oropharynx of individuals with symptoms of pharyngitis, very little is known about the prevalence of these organisms in the asymptomatic young adult population. Both *Streptococcus pyogenes* and *Staphylococcus aureus* may be present as part of the oropharyngeal environment in those not ill, however as compared to other recoverable organisms of the oropharynx they are more likely to be pathogenic. Recently we described that the prevalence of *Streptococcus pyogenes* in the oropharynx of university students with acne and, unexpectedly, the group of acne patients who were not using antibiotics and did not have symptoms of an acute upper respiratory illness had prevalence rates of *S. pyogenes* and *S. aureus* of 8.3% (4/48) and 29.8% (14/47) respectively. These rates are higher than previously reported rates of oro-pharyneal colonization in asymptomatic individuals. *S. pyogenes* has been reported to occur in between 1.3% to 50% of symptomatic individuals [2,3,4]. However, it's frequency decreases dramatically with age and for our cohort we would have expected that less than 5% of asymptomatic subjects would carry *S. pyogenes* in their pharynx. This expected rate is consistent with findings from previous investigations of asymptomatic subjects in this age group; *S. aureus* has been reported to be found in the oropharynx of 5-14% of healthy house officers. As compared to these historical rates, the findings from our previous study might suggest that acne patients have increased carriage rates of these organisms. Since the rates described above were last reported nearly 20 years ago, we felt it appropriate to determine if colonization rates have changed. We also sought to explore if there were seasonal variations in colonization.

Methods

This was an institutional review board approved cross-sectional study in which 18-27 year old students from a local university (University of Pennsylvania) had a single swab of their oropharynx. This age group was similar to that of individuals in our previous study [1]. 87 subjects were recruited during the late winter/early spring of 2002 and 100 subjects were recruited during the fall of 2002. Subjects were recruited through direct contact on campus. Subjects were excluded if they had seen a physician for acne in the past twelve months, if they had been prescribed an oral, topical or ophthalmologic antibiotic in the preceding six months, or if they had greater than ten cumulative acne lesions on facial examination. All subjects filled out a questionnaire inquiring about the presence of upper respiratory illness or symptoms during the past 30 days. Those who were swabbed during the first period were not eligible to be swabbed during the second period.

The oropharynx of subjects was swabbed with a Culturette (BD Diagnostic Systems, Cockeysville, Md.) using standard clinical technique. Within 24 hours, the specimen was processed for S. pyogenes and S. aureus according to American Society of Microbiology and National Committee for Clinical Laboratory Standards guidelines[1]. Logistic regression and chi-square analyses were used to compare dichotomous variables and P-values were reported.

Results

The overall prevalence of S. pyogenes and S. aureus was 9.6% (18/187) and 26.2% (49/187) respectively. 52 individuals reported at least one symptom that could be consistent with pharyngitis. Therefore, the overall prevalence of S. pyogenes and S. aureus in asymptomatic individuals was 8.1% (11/135) and 26.6% (36/135) respectively. The prevalence of S. pyogenes was 11.5% (10/87) during the late winter/early spring and 8% (8/100) during the fall (P=0.42) (Table 4). The prevalence of S. aureus was 27.6% (24/87) during the late winter/early spring and 25% (25/100) during the fall (P=0.69) (Table 4)

patients are, therefore, a unique and natural population of patients in whom to study the effects of long-term (>6 weeks) antibiotic use. While the effects of long-term antibiotic use on cutaneous microbial environments in acne patients have been well studied, the effects of this therapy on non-cutaneous surfaces, such as the oropharynx, which could be a source of systemic illness, have not.

Upper respiratory tract infections (URIs), such as pharyngitis, are extraordinarily common acute medical problems primarily of viral origin. In general, about 10% of URIs are likely due to a bacterial source. However, we have recently shown that nearly 35% of those with acne on acne antibiotics who had no URI symptoms were carrying Group A streptococcus in their upper airway and nearly 85% of these strains were resistant to tetracyclines. While the vast majority of URIs are not of bacterial origin, recent studies have shown that infections may be polymicriobial in that one organism facilitates the infectious capability of another. Finally, URIs are usually self-limited acute conditions, and are generally of limited consequence. However, they do have huge public health implications due to the large number of individuals afflicted. Two recent survey studies evaluated the loss of productivity in the US due to URIs defined by pharyngitis, coryza, rhinitis, and low grade temperature. Both studies estimated that more than 200 million episodes occur per year in the US and that the US economy suffers a loss of more than 25 billion dollars in annual revenue.

The inventors have demonstrated (see example 4) that antibiotic therapy for acne, when given topically and/or orally to young adults, profoundly affects an individual's likelihood of

TABLE 4

Prevalence of S. pyogenes and S. aureus in the Oropharynx of University Students At Two Different Time Points

| | S. pyogenes | | S. aureus | |
| --- | --- | --- | --- | --- |
| | Late winter/early spring prevalence (%) | Fall prevalence (%) | Late winter/early spring prevalence (%) | Fall prevalence (%) |
| All subjects | 10/87 (11.5) | 8/100 (8) | 24/87 (27.6) | 25/100 (25) |
| Subjects who reported no current illness but had recent symptoms | 4/27 (14.8) | 3/25 (12) | 7/27 (25.9) | 6/25 (24) |
| No reported illness | 6/60 (10) | 5/75 (6.7) | 17/60 (28.3) | 19/75 (25.3) |

Example 5

Acne Patients Treated with Conventional Antibiotic are Prone to Developing URI's or UTI's Concerns have been described regarding antibiotic overuse and have associated overuse with the emergence of resistant organisms, increased frequency of human exposure to pathogenic organisms, and an increase in infectious illnesses. Surprisingly, very few studies have been conducted on populations of patients who have actually been exposed to antibiotics for long periods. In fact, there are very few natural models of truly long-term human antibiotic use. If we are to understand the consequences of long-term antibiotic use, then we need a natural model of long-term use. Acne vulgaris is a model of a disease for which long-term antibiotic use is standard and appropriate therapy (1;2). Topically, both erythromycin and clindamycin are frequently used to treat acne; orally, the tetracyclines (minocycline, doxycycline, and tetracycline) and erythromycin are frequently used. Acne being colonized with GAS, an organism associated with a common acute medical iliness—pharyngitis. The example demonstrates whether the long-term use of antibiotics for acne results in an increase in a common infectious illnesses, URIs. To that end, a retrospective cohort study using the General Practice Research Database (GPRD) was carried out.

Methods

Population

The GPRD, established in the United Kingdom (UK) in 1987, is a medical records database that general practitioners (GPs) use as the primary means of tracking patient clinical information. The total population in the GPRD exceeds nine million patients with over 35 million person-years of follow-up between 1987 and 2002. About 5% of the UK population is in the GPRD, which is broadly representative of the general UK population in terms of age, sex and geographic distribution. The GPRD, which contains information on diagnoses and medications, was established with the intent of allowing researchers to conduct high quality epidemiologic studies and has been used in more than 200 peer-reviewed publications.

All information is recorded by the GP or a member of the office staff as part of the patient's medical record. Approximately 1,500 general practitioners representing 500 practices across the UK participated in the GPRD between 1987 and 2001. GPs are trained in data entry and their data are reviewed by administrators at the is GPRD to ensure that they are of sufficient quality for research studies.

Cohort and Exposure Definition

All study subjects, ranging in age between 15 and 35, were seen by a GPRD GP and, for the primary cohort study (exposure was always ascertained before determining the outcome), had a history of acne vulgaris as defined by Reed coding, which is a coding system similar to ICD-9 but hierarchical in construction. Individuals were classified as having acne and receiving acne antibiotics if, in addition to a Reed code demonstrating that they had acne, they also had British National Formulary codes consistent with the use of oral erythromycin or an oral tetracycline (e.g., doxycycline, minocycline, oxytetracycline, and tetracycline) for more than six weeks or topical erythromycin or clindamycin for more than six weeks or a combination of both. Note that this dosing interval clearly exceeds the recommended dosing used for tetracyclines for the treatment of sexually transmitted diseases and Lyme's disease. Those with Reed acne codes who did not have formulary codes consistent with acne antibiotic use as listed above were considered not exposed to acne antibiotics. All individuals were followed for 12 months from the time that they qualified for entry into their respective cohorts. We also identified another cohort of patients, in the same age range, consisting of individuals who did not have acne but did have hypertension. This illness was selected because these individuals frequently receive medical observation but are not generally believed to have an increased risk of infection. The use of this group is important as a means of assessing whether the probability of a URI diagnosis is related to the frequency of medical observation.

Outcome and Confounding Variables

Separate models were fit with to two outcomes: a URI (e.g., pharyngitis) or a URI (i.e. a common infection unlikely to be affected by the topicals used for acne) within 12 months after entering into the cohorts described above. A validation study has shown that while it is difficult to specifically determine the precise bacterial etiology of a respiratory tract infection in the GPRD, determination of the presence or absence of a respiratory tract infection is accurate in the GPRD using Reed coding similar to those used in this study.

Confounding of the association between the outcome variable and the exposure variable (i.e., acne antibiotic use) was evaluated with respect to age, year of diagnosis, gender, contraceptive use or contraceptive counseling (only for UTIs), practice, history of diabetes, and history of asthma. Visit frequency for acne (i.e., the number of office visits for acne) was also considered and the number of prescriptions for acne antibiotics during the 12 months of observation. It is noted that, because of issues related to chronology with respect to the exposure and/or the outcome, these are not strictly what would be called "risk factors." In general, the reason behind adjusting for all of these confounders was to investigate whether noted associations were due solely to more frequent visits to health care providers that might occur when an acne patient is treated with antibiotics. Thus, an attempt was made to rule out this form of ascertainment bias as an explanation for the observed associations of interest.

Statistical Analyses

Variables are described using simple percentages or means with standard deviations. In order to assess the magnitude of the associations between the acne cohorts and the onset of a URI or UTI, logistic regression models were used, with both a single independent variable in each model and multiple independent variables. The outcome of interest was any URI or UTI, as described above. If an individual had more than one infection of a given type, only the first episode was counted. Both unadjusted (single variable) and adjusted (multiple variable) odds ratios were reported with 95% confidence intervals Adjusted models included all of the confounding variables noted above. As noted in the results, the number of UTIs among men were so few that statistically proper regression analyses were not possible and are, therefore, reported for women only. All models exhibited good fit and were evaluated using routine regression diagnostic techniques. Correlation matrices of the parameter estimates were evaluated for the full model and excessive collinearity was absent in the models. Adjusted analyses included all of the confounding variables listed above. As secondary analyses, we compared our outcome risks to those among individuals who did not have acne but did have hypertension. We also subdivided acne antibiotic exposure with respect to those patients who used only topical antibiotics, oral and topical antibiotics, or only oral antibiotics.

Statistical analyses were conducted using STATA for Windows 2000 version 8.2. The GPRD dataset was manipulated using Oracle and Visual Dbase.

This study was approved by the Institutional Review Board of the University of Pennsylvania and the Scientific and Advisory Board of the Office of National Statistics of the UK.

Results 118,496 individuals with acne between 15- and 35-years-old were identified, entered into the GPRD from 1987 to 2002, of whom 84,977 (71.7%) received an acne antibiotic and 33,519 (28.3%) did not (Tables 1). Of those who used antibiotics, 6.1% used only topicals, 2.3% used only orals, and 92.6% used a combination of oral and topical antibiotics. The average age of the cohorts was 21.4 (5.76 SD) among the acne antibiotic users and 21.7 (5.74 SD) among the acne antibiotic non-users. The median age of the cohorts was 19 (25%—17, 75%—26) among the acne antibiotic users and 20 (25%—17, 75%—26) among the acne antibiotic non-users. In addition, 44,725 (52.6%) of the acne antibiotic users were female and 21,507 (64.1%) of the non-users were female. Additional baseline information is shown in Table 1. Within the first year of study observation, 18,281 (15.4%) had at least one URI that was diagnosed by a GP and 4,270 (3.6%) had a UTI diagnosed by a GP. The odds ratio of developing a URI among those on antibiotics as compared to those not on antibiotics within the first year of observation was 2.15 (2.05, 2.23, p<0.0001). The odds ratio of developing a UTI for women among those on antibiotics was 1.11 (1.03, 1.19 p=0.002)) as compared to those not on antibiotics within the first year of observation.

Using multivariable logistic regression, the odds ratio of developing a URI among those on antibiotics as compared to those not on antibiotics within the first year of observation was 2.23 (2.12, 2.34, p<0.001). This model was adjusted by gender, age, year of diagnosis, practice, number of prescriptions for acne antibiotics over the 12 months of observation, number of office visits for acne, history of diabetes, and history of asthma. The difference between this odds ratio of association of the adjusted and unadjusted model is about 12%. This difference is likely not statistically or clinically important, so we will use the unadjusted ratio of 2.15 for the rest of this report (20). Furthermore, individuals were classified separately into non-users, users of only topical antibiotics, users of oral and topical antibiotics, and users of only oral antibiotics. The odds ratios for the association as compared to the non-users were 2.37 (2.12, 2.64) (topical only); 1.88 (1.80, 1.96) (topical and oral); and 2.75 (2.37, 3.18) (oral only). No interactions were noted between gender, age, frequency of acne associated office visits, and the use of acne antibiotics, and URI. Finally, to ensure that the increased association of URI with acne antibiotic use was not due to an increased frequency of office visits, we compared the rate of URI among those aged 15 to 35 in the GPRD with another underlying diagnosis requiring somewhat frequent care, i.e., hypertension among those aged 15 to 35 in the GPRD who did not have a diagnosis of acne. The rate of URI among those in the hypertension cohort was 7.9% (1,653 cases of URI among 20,871 individuals with hypertension). The odds ratio comparing the acne antibiotic non-users to the hypertension cohort, adjusted for age and gender was 0.97 (0.93, 1.01) and the odds ratio comparing the acne antibiotic users to the hypertension cohort was 2.12 (2.00, 2.27).

Due to the rarity of UTI, (33 men who used antibiotics and had a UTI) multivariable regression models were not possible for men. Using multivariable logistic regression for women only, the odds ratio of developing a UTI among those with acne on antibiotics as compared to those with acne not on antibiotics within the first year of observation was 1.10 (1.01, 1.19 p=0.02). This model was adjusted by gender, age, number of prescriptions for acne antibiotics over the 12 months of observation, year of diagnosis, number of office visits for acne, contraceptive use, history of diabetes, history of hypertension, and history of asthma. The odds ratio of association changed minimally as compared to the unadjusted model, indicating that confounding was unlikely to be important (20). In addition the magnitude of either the adjusted or unadjusted odds ratio is unlikely to be of clinical importance. This lack of clinical and statistical association comparing acne antibiotic users and non-users was confirmed when we compared the antibiotic users to those with hypertension, which again revealing no association with urinary track infections (1.09 (0.91, 1.30), p=0.34).

The foregoing has been a description of certain non-limiting embodiments of the invention. Those of ordinary skill in the art will appreciate that various changes and modifications to this description may be made without departing from the spirit or scope of the present invention, as defined in the following claims.

What is claimed is:

1. A method of treating an acne in a subject, the method comprising: administering to said subject, an effective amount of a bacteriocin-like inhibitory substance (BLIS) isolated from *Streptococcus salivarius*, thereby treating said acne in said subject.

2. The method of claim 1, wherein the BLIS is SAL A2, SAL B, or a combination thereof.

3. A method of treating an acne in a subject, the method comprising: administering to said subject a composition comprising an effective amount of a bacteriocin-like inhibitory substance (BLIS) isolated from *Streptococcus salivarius*, wherein the composition further comprises BLIS derived from *S. aureus, P. acnes, B. melaninogenicus*, or a combination thereof.

4. The method of claim 1, further comprising coadministering to said subject an additional agent, wherein the agent is isotrenitoin, Benzoyl peroxide, topical retinoid, spironolactone, an oral contraceptive or a combination thereof.

5. The method of claim 1, wherein said acne is caused by a bacteria resistant to erythromycin, tetracycline, doxycycline, minocycline, oxytetracycline clindamycin, or a combination thereof.

6. A method of treating an acne in a subject, the method comprising administering to said subject an effective amount of a pharmaceutical preparation comprising a bacteriocin-like inhibitory substance (BLIS) from *Streptococcus salivarius*, whereby said BLIS is bacteriocidal or bacteriostatic for bacteria causing said acne thereby treating said acne in said subject.

7. The method according to claim 6, wherein said administering comprises orally administering to said subject a liquid or solid formulation containing said pharmaceutical preparation.

8. The method according to claim 6, wherein said administering comprises topically administering to said subject a formulation containing said pharmaceutical preparation.

9. The method according to claim 6, wherein said administering comprises administering to said subject a formulation containing said pharmaceutical preparation, wherein said formulation is a food formulation.

10. The method of claim 9, wherein said food formulation is a yoghurt culture.

11. The method according to claim 6, wherein said administering comprises administering to said subject a formulation containing said pharmaceutical preparation, wherein said formulation is a probiotic capsule.

12. The method of claim 6, further comprising a pharmaceutically acceptable carrier, excipient, flow agent, processing aid, a diluent or a combination thereof.

13. The method of claim 12, wherein said carrier, excipient, lubricant, flow agent, processing aid, diluent or a combination thereof, is a gum, a starch, a sugar, a cellulosic material, an acrylate, calcium carbonate, magnesium oxide, talc, lactose monohydrate, magnesium stearate, colloidal silicone dioxide or mixtures thereof.

14. The method of claim 6, wherein said pharmaceutical preparation is in the form of a pellet, a tablet, a capsule, a solution, a suspension, a dispersion, an emulsion, an elixir, a gel, an ointment, a cream, a foam or a suppository.

15. The method of claim 6, wherein said pharmaceutical preparation is a liquid dosage form.

16. The method of claim 6, wherein said pharmaceutical preparation is a solid dosage form.

17. The method of claim 6, wherein treating is preventing, reducing incidence of, inhibiting, reducing symptoms or their severity or a combination thereof.

18. A method of suppressing, inhibiting the growth of, or killing a *P. acnes* bacteria comprising the step of contacting said bacteria with a bacteriocin-like inhibiting substance (BLIS), wherein said BLIS is a bacteriocide or a bacteriostat of *P. acnes*, and wherein said BLIS is isolated from *Streptococcus salivarius*.

* * * * *

UNITED STATES PATENT AND TRADEMARK OFFICE
CERTIFICATE OF CORRECTION

PATENT NO. : 8,415,289 B2
APPLICATION NO. : 12/086335
DATED : April 9, 2013
INVENTOR(S) : David Margolis et al.

It is certified that error appears in the above-identified patent and that said Letters Patent is hereby corrected as shown below:

In the Specification

In column 1, please replace lines 16-19 with the following:

--This invention was made with government support under Grant Number K24 AR02212, awarded by the National Institutes of Health and grant number HS10399 awarded by AHRQ (Agency for Healthcare Research and Quality). The government has certain rights in the invention.--

Signed and Sealed this
Fifth Day of November, 2013

Teresa Stanek Rea
*Deputy Director of the United States Patent and Trademark Office*

```
                              SEQUENCE LISTING

<160> NUMBER OF SEQ ID NOS: 4

<210> SEQ ID NO 1
<211> LENGTH: 22
<212> TYPE: PRT
<213> ORGANISM: Streptococcus salivarius

<400> SEQUENCE: 1

Lys Arg Gly Ser Gly Trp Ile Ala Thr Ile Thr Asp Asp Cys Pro Asn
1               5                   10                  15

Ser Val Phe Val Cys Cys
            20

<210> SEQ ID NO 2
<211> LENGTH: 22
<212> TYPE: PRT
<213> ORGANISM: Streptococcus salivarius

<400> SEQUENCE: 2

Lys Lys Gly Ser Gly Trp Phe Ala Thr Ile Thr Asp Asp Cys Pro Asn
1               5                   10                  15

Ser Val Phe Val Cys Cys
            20

<210> SEQ ID NO 3
<211> LENGTH: 22
<212> TYPE: PRT
<213> ORGANISM: Streptococcus salivarius

<400> SEQUENCE: 3

Lys Arg Gly Thr Gly Trp Phe Ala Thr Ile Thr Asp Asp Cys Pro Asn
1               5                   10                  15

Ser Val Phe Val Cys Cys
            20

<210> SEQ ID NO 4
<211> LENGTH: 25
<212> TYPE: PRT
<213> ORGANISM: Streptococcus salivarius
```

```
<400> SEQUENCE: 4

Gly Gly Gly Val Ile Gln Thr Ile Ser His Glu Cys Arg Met Asn Ser
1               5                   10                  15

Trp Gln Phe Leu Phe Thr Cys Cys Ser
            20              25
```